United States Patent
Loebertmann et al.

(10) Patent No.: US 11,033,649 B2
(45) Date of Patent: Jun. 15, 2021

(54) ODOR CONTROL PRODUCT PACKAGE AND METHOD OF FORMING THE SAME

(71) Applicant: SATELLITE INDUSTRIES, INC., Minneapolis, MN (US)

(72) Inventors: Douglas E. Loebertmann, Georgetown, TX (US); Daniel D. Phothirath, Austin, TX (US); Stephen A. Heyer, Austin, TX (US)

(73) Assignee: Satellite Industries, Inc., Minneapolis, MN (US)

( * ) Notice: Subject to any disclaimer, the term of this patent is extended or adjusted under 35 U.S.C. 154(b) by 325 days.

(21) Appl. No.: 16/378,100

(22) Filed: Apr. 8, 2019

(65) Prior Publication Data

US 2019/0231914 A1   Aug. 1, 2019

Related U.S. Application Data

(62) Division of application No. 15/287,256, filed on Oct. 6, 2016, now Pat. No. 10,251,966.

(Continued)

(51) Int. Cl.
*A61L 9/012* (2006.01)
*B65B 9/02* (2006.01)
(Continued)

(52) U.S. Cl.
CPC ............... *A61L 9/012* (2013.01); *B65B 3/02* (2013.01); *B65B 3/04* (2013.01); *B65B 9/023* (2013.01);
(Continued)

(58) Field of Classification Search
CPC ........... B65B 9/023; B65B 3/02; A61L 9/012; B65D 65/46; B65D 75/30
See application file for complete search history.

(56) References Cited

U.S. PATENT DOCUMENTS 3,057,127 A   10/1962   Gex et al.
3,218,776 A   11/1965   Cloud
(Continued)

FOREIGN PATENT DOCUMENTS

DE   102014206095 A1   10/2015
EP   2179748 A1   4/2010
(Continued)

OTHER PUBLICATIONS

The International Search Report and Written Opinion rendered by the International Searching Authority for PCT/US16/55740, dated Feb. 2, 2017, 10 pages.

*Primary Examiner* — Kevin Joyner
(74) *Attorney, Agent, or Firm* — Skaar Ulbrich Macari, P.A.

(57) ABSTRACT

A hybrid packet containing deodorizing chemicals can dissolve to release the chemicals in a brine solution while still being formed using high speed packet forming machinery. A hybrid packet can be formed by feeding a sheet of dissolvable paper and a film of PVA material into the packet forming machine to form a hybrid packet having one side formed of the paper and the opposing side formed of the PVA material. The PVA sheet and paper panels are fused together by the machine to form a sealed interior compartment that holds the deodorizing chemicals. A serrated knife edge can be used to pierce the paper and PVA layers to separate individual packets. Reduced water volume in the forming operation avoids compromising the dissolvable paper portion of the hybrid packet. The packet contents can include citric acid and sodium bicarbonate.

20 Claims, 7 Drawing Sheets

Related U.S. Application Data

(60) Provisional application No. 62/237,918, filed on Oct. 6, 2015.

(51) Int. Cl.

| | | |
|---|---|---|
| *B65D 65/46* | (2006.01) | |
| *B65B 3/02* | (2006.01) | |
| *B65D 75/30* | (2006.01) | |
| *B65B 61/08* | (2006.01) | |
| *B65B 3/04* | (2006.01) | |
| *B65B 9/20* | (2012.01) | |
| *B65B 41/10* | (2006.01) | |
| *B65B 47/02* | (2006.01) | |
| *B65B 51/16* | (2006.01) | |
| *B65B 61/06* | (2006.01) | |
| *B65D 75/42* | (2006.01) | |
| *B65D 75/52* | (2006.01) | |

(52) U.S. Cl.
CPC ............... *B65B 9/20* (2013.01); *B65B 41/10* (2013.01); *B65B 47/02* (2013.01); *B65B 51/16* (2013.01); *B65B 61/06* (2013.01); *B65B 61/08* (2013.01); *B65D 65/46* (2013.01); *B65D 75/30* (2013.01); *B65D 75/42* (2013.01); *B65D 75/527* (2013.01)

(56) References Cited

U.S. PATENT DOCUMENTS

| | | | |
|---|---|---|---|
| 3,724,002 A | | 4/1973 | Buck |
| 3,879,917 A | | 4/1975 | Bassendale |
| 4,522,738 A | | 6/1985 | Magid et al. |
| 4,794,665 A | | 1/1989 | Peters |
| 4,806,261 A | * | 2/1989 | Ciallella ............ C11D 17/044 510/296 |
| 5,578,023 A | | 11/1996 | Schneider |
| 6,966,166 B2 | | 11/2005 | Kissling |
| 7,127,874 B2 | | 10/2006 | Viltro et al. |
| 2002/0187119 A1 | | 12/2002 | Greer et al. |
| 2003/0108705 A1 | | 6/2003 | Duffield et al. |
| 2015/0197433 A1 | | 7/2015 | Martin |

FOREIGN PATENT DOCUMENTS

| | | |
|---|---|---|
| JP | 2003049396 A | 2/2003 |
| WO | 2008100993 A1 | 8/2008 |

\* cited by examiner

ODOR CONTROL PRODUCT PACKAGE AND METHOD OF FORMING THE SAME

PRIORITY

This application is a divisional of U.S. patent application Ser. No. 15/287,256, filed Oct. 6, 2016, which claims the priority benefit of U.S. Provisional Application No. 62/237,918, filed on Oct. 6, 2015, and wherein each of the foregoing applications is hereby incorporated herein by reference in its entirety.

FIELD

The present invention relates generally to portable restrooms, and more particularly to packaging of odor control substances for use in portable restrooms.

BACKGROUND

Portable restrooms such as disclosed in U.S. Pat. No. 7,975,325, entitled PORTABLE TOILET, and fully incorporated herein, are known. Controlling odors from the waste tank in the portable toilet is important to the restroom user's experience. Odors are typically controlled by adding chemicals to the waste tanks. These chemicals can contain deodorants, colorants, bacterial control compounds and other substances. Odor control chemicals typically come in liquid, tablet and powdered forms.

Powdered odor control chemicals are available in convenient single-use packets or pouches. The person servicing the portable restroom simply drops a packet/pouch into the waste tank. The packet then dissolves and releases the powdered chemicals into the tank liquid.

The packets or pouches are formed of either a dissolving paper or of a dissolving plastic material. The plastic material is typically a polyvinyl alcohol (PVA) material, which is a water soluble polymer.

The paper packets are formed using typical vertical or horizontal form fill seal packaging machines that can produce approximately 50 finished packets per minute. In contrast, the PVA packets can be formed using high speed rotary packaging equipment to form more than 500 packets per minute. Thus, PVA packets are much less costly to produce.

However, PVA packets do not dissolve in brine solutions. In cold climates in the winter months, operators of portable toilets will use a brine solution in the waste tank in order to guard against freezing of the waste liquid. Operators must, therefore, use the more expensive paper pouches for at least part of the year, or switch to inconvenient liquid deodorizers. Thus, there is a need to provide an improved single-use deodorizer package that can be manufactured with high speed pouch forming machinery and that can release the contained deodorizing chemicals upon introduction to a brine solution.

SUMMARY

The present invention, in certain embodiments, provides a hybrid packet containing deodorizing chemicals that can dissolve to release the chemicals in a brine solution while still being formed using high speed packet forming machinery. A hybrid packet can be formed by feeding a sheet of dissolvable paper and a film of PVA material into the packet forming machine to form a hybrid packet having one side formed of the paper and the opposing side formed of the PVA material. The PVA sheet and paper panels are fused together by the machine to form a sealed interior compartment that holds the deodorizing chemicals. A serrated knife edge can be used to pierce the paper and PVA layers to separate individual packets. Reduced water volume in the forming operation avoids compromising the dissolvable paper portion of the hybrid packet. The packet contents can include citric acid and sodium bicarbonate.

The disclosure includes a packet assembly containing deodorizer. The packet assembly includes a water soluble paper sheet and a polyvinyl alcohol (PVA) film sealed against the water soluble paper sheet. The sealed PVA film against the paper sheet defines a first sealed compartment between the water soluble paper sheet and the PVA film. A deodorizer material is disposed inside of the first sealed compartment.

The deodorizer material can include citric acid and sodium bicarbonate. The deodorizer material can be in a liquid form at room temperature, a granular form or other forms as explained herein.

The sealing of the PVA film against the water soluble paper sheet can define a second sealed compartment, a third sealed compartment, etc. The deodorizer material is disposed inside of each of the sealed compartments. A serrated score line is defined between each of the sealed compartments.

The disclosure further includes a method of manufacturing deodorizer-containing packets with a high speed packet forming machine. The method includes feeding a sheet of water soluble paper into the high speed packet forming machine, feeding a film of PVA into the high speed packet forming machine, forming a series of sealed pockets between the film of PVA and the sheet of water soluble paper by applying heat to the PVA film while pressing the PVA film against the water soluble paper sheet, and filling each pocket in the series of pockets with a deodorizer material.

A heated pressure roller can be used to heat and press the PVA film against the water soluble paper. A sealing roller can be used to heat and press against the water soluble paper. Separate packets can be formed creating a serrated score line between adjacent pockets in the series of pockets. The score line can be formed by piercing through each of the PVA film and water soluble paper sheet with a serrated knife edge.

A rotating drum can be provided with a plurality of serrated edge blades mounted longitudinally along the outer circumferential surface of the drum. Rotating the drum during the forming process pierces through a sealed portion of the PVA film and water soluble paper sheet located between adjacent pockets to define separate packets with a serrated score line between adjacent pockets in the series of pockets.

The PVA film and water soluble paper sheet can be provided in roll form for feeding into the high speed packet forming machinery. The operating speed of the high speed forming machinery can be set to produce at least 500 deodorizer-containing packets per minute. The moisture volume typically used in a high speed packet forming operation can be reduced by approximately 20%.

The disclosure also includes a system for producing deodorizer-containing packets. The system includes a high speed packet forming machine. A roll of PVA film is disposed in the machine. A roll of water soluble paper is disposed in the machine. A hopper filled with a deodorizer material is provided to the machine. A heated pressure roller is disposed in the machine and configured to heat and press a feed of PVA film from the roll of PVA film against a sheet of water soluble paper from the roll of water soluble paper.

A sealing roller is disposed in the machine and configured to heat and press against the sheet of water soluble paper from the roll of water soluble paper.

The above summary is not intended to limit the scope of the invention, or describe each embodiment, aspect, implementation, feature or advantage of the invention. The detailed technology and preferred embodiments for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
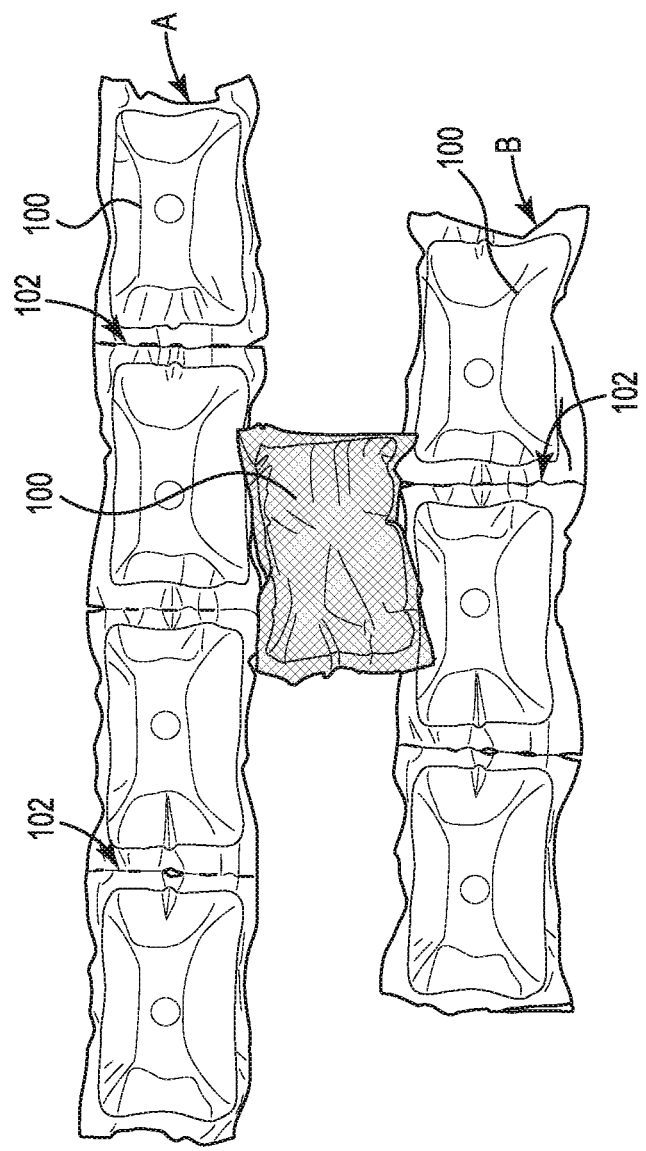
FIG. 1 is an image of hybrid pouches according to certain embodiments.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

In the following descriptions, the present invention will be explained with reference to various exemplary embodiments. Nevertheless, these embodiments are not intended to limit the present invention to any specific example, environment, application, or particular implementation described herein. Therefore, descriptions of these example embodiments are only provided for purpose of illustration rather than to limit the present invention.

Referring to FIG. 1, several hybrid packet/pod/packages 100 (hereinafter referred to as a packet) are shown. One side of each packet is formed using PVA sheet material and the opposing side is formed with a dissolving paper sheet. The PVA sheet and paper panels are fused together in a high speed packet forming machine to form a sealed interior compartment that holds the deodorizing chemicals.

Serrations 102 are formed between adjacent packets 100 so that individual packets can be separated for packaging purposes and/or for introducing individually to the waste tank of the portable restroom.

The top and bottom rows A and B of the packets shown in FIG. 1 are each a series of individual packets 100 separated by serration lines 102 between adjacent packets. In each of rows A and B, the side facing upwards is the PVA layer and the paper layer is facing downwards. Typically the PVA layer is clear, but can be colored and/or opaque as well.

A single packet 100 is shown between rows A and B. This single packet is flipped over as compared to the orientation of the rows of packets so that the paper side can be seen. The PVA layer is facing downwards. The paper layer is not transparent. Text and/or images can be printed on the paper layer before or after the packet is formed.

The paper material forming the paper layer dissolves when exposed to water, including brine solutions. The PVA does not dissolve in brine. However, that is not a problem for the hybrid packet because the paper material dissolves sufficiently in brine solutions to release the odor-reducing chemicals into the waste tank liquid. One suitable paper material is water soluble paper commercially available from companies such as AQUASOL CORP.

Figure 5:
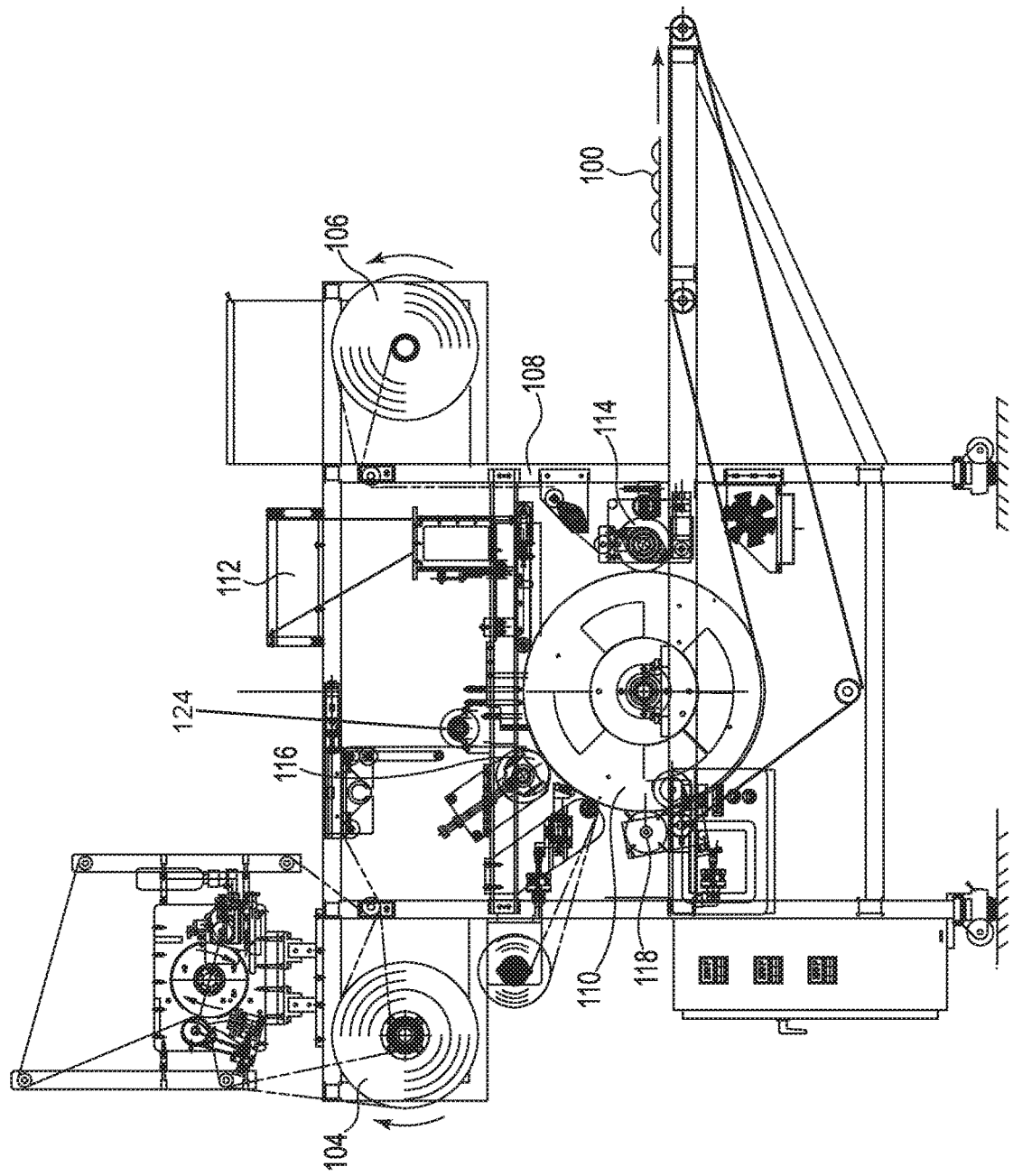
FIG. 5 is a front view of a high speed packet forming machine for the hybrid packets according to certain embodiments.
Figure 6:
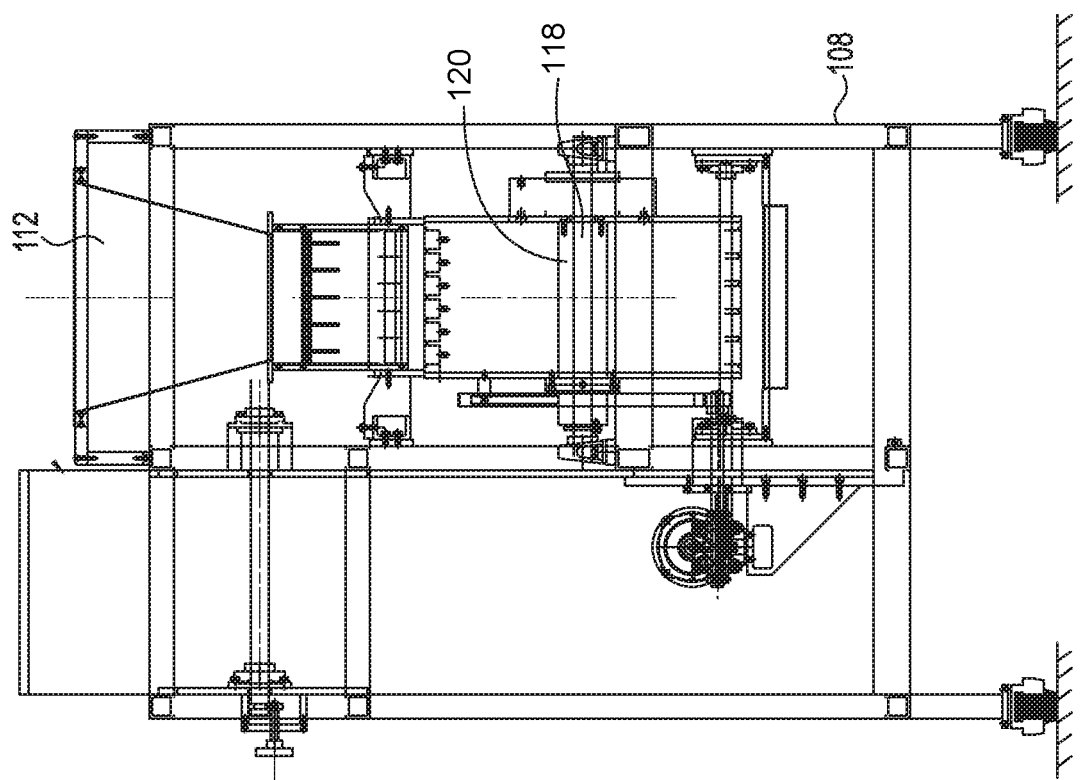
FIG. 6 is a side view of the packet forming machine of FIG. 5.
Figure 7:
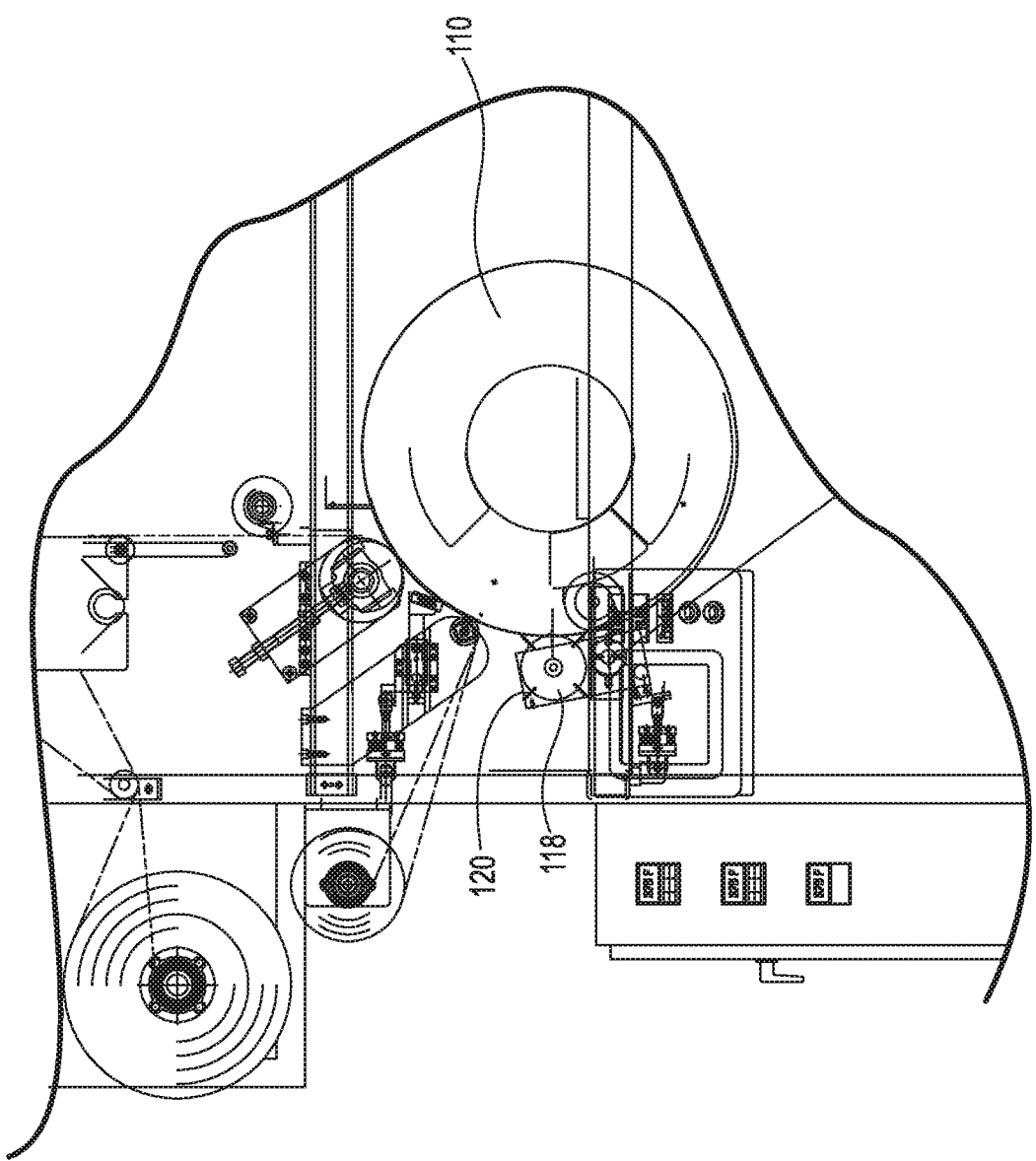
FIG. 7 is a detail view of the packet forming machine of FIG. 5.

In another aspect, the packets 100 are formed according to a unique forming method. High speed forming machinery (e.g. from MATTPAK, INC. and CLOUD PACKAGING EQUIPMENT) is utilized. Referring to FIGS. 5-7, a roll of paper sheet 104 material is brought together with a roll of PVA sheet 106 material in the high speed packet forming machine 108. The respective material sheets 104 and 106 are fed into the machine 108 from respective long rolls of the respective materials as shown in FIG. 5.

The PVA film material 104 and water soluble paper material, from their respective spools 104, 106, are fed into the rotating forming drum 110 of the forming machine 108. The paper and PVA films are heated and pressed together with a cavity formed therebetween, and the deodorizing chemical is filled into that cavity from the material hopper 112. In greater detail, the PVA film is heated and pressed via a heated pressure roller 114, and the paper sheet material is heated and pressed to seal against the PVA film via a sealing roller 116.

Then, through the application of pressure, heat and moisture applied by the packet forming machine 108, the upper paper 104 and lower PVA 106 layers are fused together, without applying an additional adhesive, to form a series of sealed packets. The chemicals are filled into the packets as they are formed.

Figure 2:
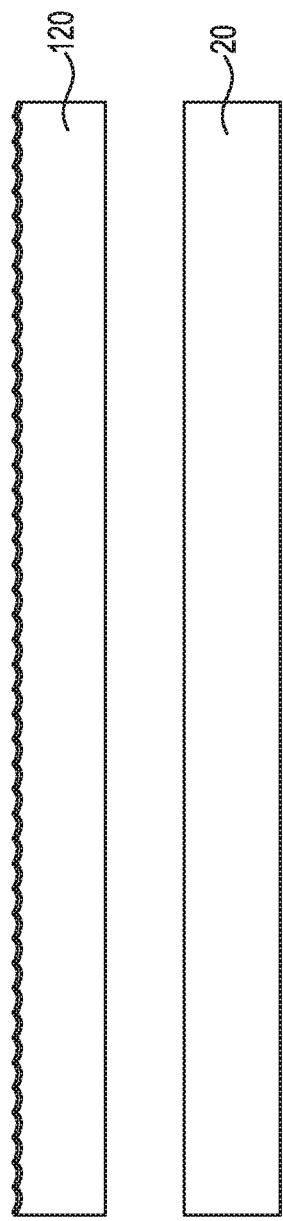
FIGS. 2-4 are images of a serrated knife blade for a high speed pouch forming machine according to certain embodiments shown next to a conventional blade for such machine.
Figure 3:
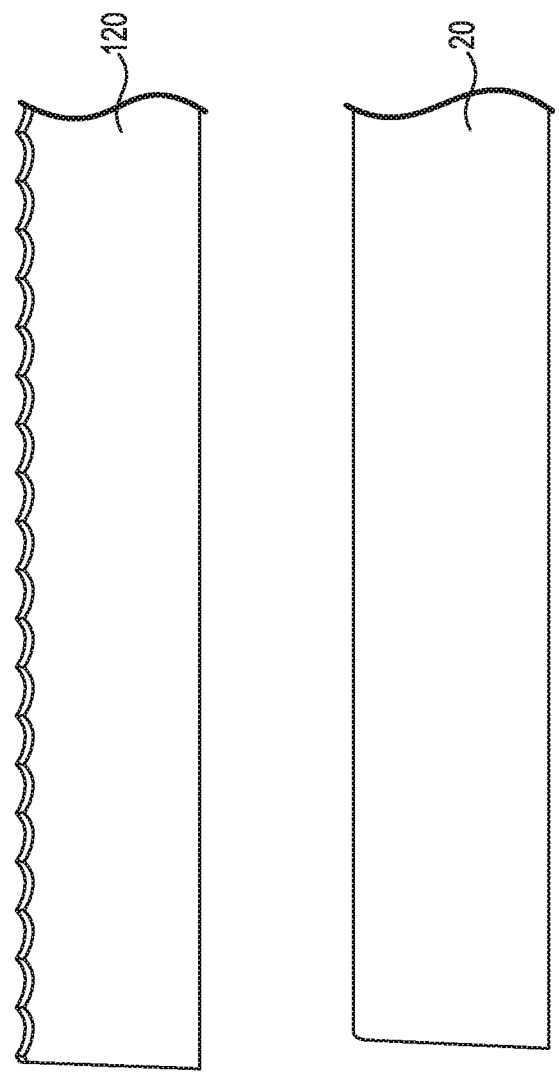
Figure 4:
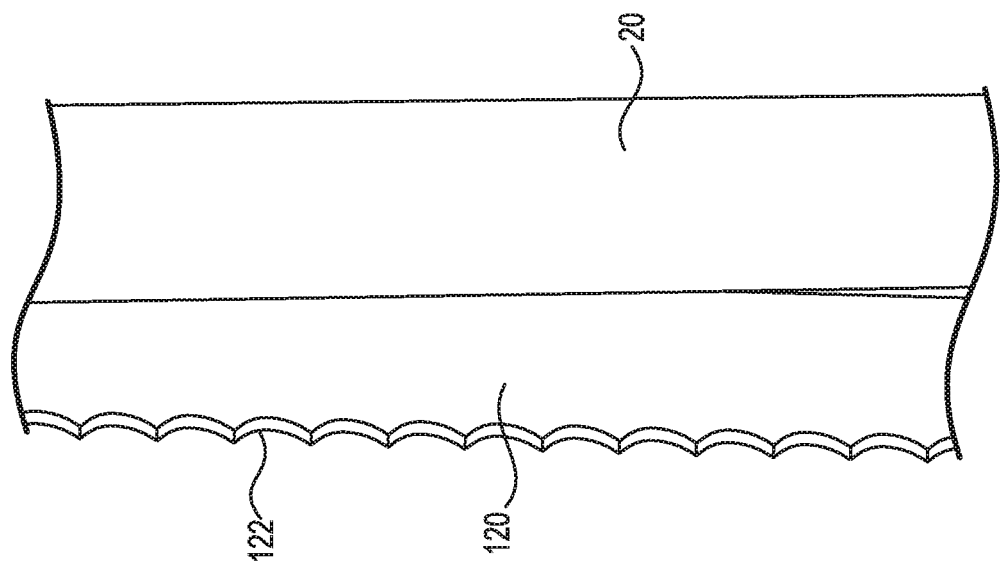

Also, as the packets are being formed by the rotating drum 110, a cutting drum 118 rotates about an axis perpendicular to the packet forming direction. Referring to the detail view of FIG. 7, a plurality of blades 120 are mounted longitudinally along the drum's outer circumferential surface. The blades 120 serve to divide the individual packets by making a serration line between adjacent packets as a result of having a serrated edge 122 as can be seen in FIGS. 2-4. The blade 120 can be used to either form a score line between adjacent packets 100 in a series of packets, or the blade 120 can completely cut through the material web between adjacent packets 100 to physically separate apart the individual packets 100.

A typical straight edge blade 20 is shown in FIG. 2 next to a serrated edge blade 120 according to one embodiment of the invention. FIGS. 3-4 show close-ups of both blades 120 and 20. The serrated edge 122 is clearly seen as being formed along one longitudinal edge of the blade 120. In an alternative, the cutting edge can be configured with a sawtooth profile instead of the scalloped serrations. In both the serrated and sawtooth embodiments, the cutting edge comprises a series of alternating peaks and valleys that define a plurality of sharp points and edges. Other cutting edge configurations that provide the plurality of sharp points and edges can also be employed.

Typical high speed forming machinery employs straight edge blades 20 because a straight edge is adequate for separating individual PVA packets. A straight edge will not adequately pierce the paper material, but paper sheet is not used in these high speed forming machines. However, the serrated edge blade 120 will separate the individual hybrid packets 100 with a serration line. Therefore, in another aspect, the high speed forming machine is modified with serrated blades 120 in place of the conventional straight edge blades 20. As noted above, FIG. 1 shows the results of the serrated blades forming lateral serration lines 102 at the approximate mid-point between adjacent packets.

In yet another aspect of certain embodiments, the moisture volume typically used in the packet forming operation of the high speed packeting machinery is reduced to approximately 80% of normal (i.e., a 20% reduction). Too much moisture would compromise the dissolvable paper panel's integrity. The Applicant has determined that the approximate 80% figure allows the paper and PVA panels to be successfully joined to form the hybrid packets 100 without damaging or compromising the paper panel portion of the hybrid packets.

The water reduction can be accomplished by reducing the speed of the wetting roller 124 as shown in FIG. 24. The wetting roller 124 is formed of a porous material, such as felt, which soaks up water as it rotates in a water bath and then contacts the paper sheet to apply water to it. Reducing the velocity of this roller reduces the volume of water being applied to the paper sheet during the forming process.

Multiple individual packets can be packaged together in a variety of commercial packaging configurations.

Production rates of over 500 packets per minute can be achieved using the techniques disclosed herein. This speed is approximately the same as conventional PVA packet forming rates and is more than ten times faster than conventional paper packet forming rates. Of course, both higher and lower operating speeds can also be employed. For example, the production rate can be set to 600 packets per minute, 400 packets per minute, 300 packets per minute, etc.

The deodorizing chemicals or substances contained within the hybrid packets 100 can be in the form of a powder, granules, tablet, gel or liquid, or a combination thereof. The hybrid packet 100 can also be formed with multiple separate pockets in a given individual packet so that different chemicals or substances can be kept separate until released into the waste tank.

The chemical contents of the hybrid packet 100 according to certain embodiments can include citric acid and sodium bicarbonate. These chemicals produce a fizzing action when introduced to water. The fizzing action helps to disperse the odor-reducing chemicals in the waste tank. This was not previously possible with wholly-PVA packets because the citric acid and sodium bicarbonate chemical would inhibit dissolving of the PVA in the water.

Other features and aspects of the invention can be appreciated from the depictions in the figures, even if not described in writing herein.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. A packet assembly containing deodorizer, comprising:
a water soluble paper sheet;
a polyvinyl alcohol (PVA) film sealed against the water soluble paper sheet which defines a first sealed compartment between the water soluble paper sheet and the PVA film; and
a deodorizer material disposed inside of the first sealed compartment.

2. The packet assembly of claim 1, wherein the deodorizer material includes citric acid and sodium bicarbonate.

3. The packet assembly of claim 1, wherein the deodorizer material is in a liquid form at room temperature.

4. The packet assembly of claim 1, wherein the deodorizer material is in a granular form.

5. The packet assembly of claim 1, wherein the sealing of the PVA film against the water soluble paper sheet defines a second sealed compartment, wherein the deodorizer material is disposed inside of the second sealed compartment, and wherein a serrated score line is defined between the first and second sealed compartments.

6. The packet assembly of claim 1, wherein the water soluble paper sheet is not transparent.

7. A packet assembly containing deodorizer, comprising:
a water soluble paper sheet;
a PVA film sealed against the water soluble paper sheet which
defines a plurality of sealed compartments between the water soluble paper sheet and the PVA film; and
a deodorizer material disposed inside of each of the sealed compartments.

8. The packet assembly of claim 7, wherein the deodorizer material includes citric acid and sodium bicarbonate.

9. The packet assembly of claim 7, wherein the deodorizer material is in a liquid form at room temperature.

10. The packet assembly of claim 7, wherein the deodorizer material is in a granular form.

11. The packet assembly of claim 7, wherein a serrated score line is defined between adjacent sealed compartments of the packet assembly.

12. The packet assembly of claim 7, wherein the water soluble paper sheet is not transparent.

13. The packet assembly of claim 7, wherein plurality of sealed compartments are serially arranged as a linear strip.

14. A packet assembly containing deodorizer, comprising:
a water soluble paper sheet;
a water-soluble polymer film sealed against the water soluble paper sheet which
defines a first sealed compartment between the water soluble paper sheet and the water-soluble polymer film; and
a deodorizer material disposed inside of the first sealed compartment.

15. The packet assembly of claim 14, wherein the deodorizer material includes citric acid and sodium bicarbonate.

16. The packet assembly of claim 14, wherein the deodorizer material is in a liquid form at room temperature.

17. The packet assembly of claim 14, wherein the deodorizer material is in a granular form.

18. The packet assembly of claim 14, wherein the sealing of the water-soluble polymer film against the water soluble paper sheet defines a second sealed compartment, wherein the deodorizer material is disposed inside of the second sealed compartment, and wherein a serrated score line is defined between the first and second sealed compartments.

19. The packet assembly of claim 14, wherein the water soluble paper sheet is not transparent.

20. The packet assembly of claim 14, wherein the water-soluble polymer film is sealed directly against the water soluble paper sheet without an additional adhesive.

* * * * *